US009541499B2

(12) United States Patent
Ikeda

(10) Patent No.: US 9,541,499 B2
(45) Date of Patent: Jan. 10, 2017

(54) PACKAGE INSPECTION SYSTEM

(71) Applicant: System Square Inc., Nagaoka-shi, Niigata-ken (JP)

(72) Inventor: Noriaki Ikeda, Nagaoka (JP)

(73) Assignee: SYSTEM SQUARE INC., Nagaoka-Shi (JP)

(*) Notice: Subject to any disclaimer, the term of this patent is extended or adjusted under 35 U.S.C. 154(b) by 0 days.

(21) Appl. No.: 14/680,460

(22) Filed: Apr. 7, 2015

(65) Prior Publication Data
US 2015/0241341 A1 Aug. 27, 2015

Related U.S. Application Data

(63) Continuation of application No. PCT/JP2013/076983, filed on Oct. 3, 2013.

(30) Foreign Application Priority Data

Oct. 17, 2012 (JP) .................................. 2012-229565

(51) Int. Cl.
*G01N 21/3581* (2014.01)
*G01N 21/90* (2006.01)
(Continued)

(52) U.S. Cl.
CPC .......... *G01N 21/3581* (2013.01); *B65B 57/10* (2013.01); *G01N 21/84* (2013.01); *G01N 21/90* (2013.01);
(Continued)

(58) Field of Classification Search
CPC .... G01N 21/3581; G01N 21/84; G01N 23/10; G01N 21/90; G01N 2021/845; G01N 33/02; H04N 5/33; H04N 5/32; G01V 5/0016
(Continued)

(56) References Cited

U.S. PATENT DOCUMENTS 5,901,198 A * 5/1999 Crawford ............... G01V 5/005
378/15
5,949,842 A * 9/1999 Schafer ................. G01V 5/005
378/15
(Continued)

FOREIGN PATENT DOCUMENTS

CN 101802595 A 8/2010
JP U-S58-17544 7/1956
(Continued)

OTHER PUBLICATIONS

International Search Report issued in corresponding application PCT/JP2013/076983, dated Jan. 7, 2014, pp. 1-5.
(Continued)

*Primary Examiner* — David Porta
*Assistant Examiner* — Gisselle Gutierrez
(74) *Attorney, Agent, or Firm* — Brinks Gilson & Lione

(57) ABSTRACT

A package inspection system includes a conveyor mechanism 6, an X-ray generator 10 applying X rays to a package W1 conveyed by the conveyor mechanism 6, an X-ray sensor 13, and an optical sensor 15. First image data showing the outline of the content of the package W1 are generated based on detection output from the X-ray sensor 13. Second image data showing the outline of the wrapping of the package W1 are generated based on detection output from an optical sensor 15. The relative position of the wrapping and the content is determined based on the first and second image data, so that failures, e.g., the content caught in a seal of the wrapping can be detected accurately. The package inspection system can accurately determine a position of a wrapping and the content of a package even if a package has a light non-transmissive wrapping.

12 Claims, 13 Drawing Sheets

(51) Int. Cl.
    *G01N 23/10*    (2006.01)
    *G01N 21/84*    (2006.01)
    *G01V 5/00*    (2006.01)
    *H04N 5/32*    (2006.01)
    *H04N 5/33*    (2006.01)
    *B65B 57/10*    (2006.01)
    *G01N 33/02*    (2006.01)

(52) U.S. Cl.
    CPC .............. *G01N 23/10* (2013.01); *G01V 5/0016* (2013.01); *H04N 5/32* (2013.01); *H04N 5/33* (2013.01); *G01N 33/02* (2013.01); *G01N 2021/845* (2013.01)

(58) Field of Classification Search
    USPC .......................................... 250/338.1; 378/57
    See application file for complete search history.

(56) References Cited

U.S. PATENT DOCUMENTS

| | | | | |
|---|---|---|---|---|
| 6,256,404 | B1 * | 7/2001 | Gordon | G01V 5/005 378/57 |
| 6,324,253 | B1 * | 11/2001 | Yuyama | G01N 23/04 209/589 |
| 8,483,475 | B2 | 7/2013 | Kabumoto et al. | |
| 2007/0009085 | A1 | 1/2007 | Otani et al. | |
| 2007/0164222 | A1 | 7/2007 | Biel et al. | |
| 2009/0080706 | A1 * | 3/2009 | Tao | G01N 21/94 382/110 |
| 2012/0327227 | A1 * | 12/2012 | Ikeda | G01M 3/38 348/143 |

FOREIGN PATENT DOCUMENTS

| | | |
|---|---|---|
| JP | A-54-158984 | 12/1979 |
| JP | A-H05-322803 | 7/1993 |
| JP | 6-281598 A | 10/1994 |
| JP | A-09-127017 | 5/1997 |
| JP | A-2004-340583 | 12/2004 |
| JP | A-2005-031069 | 2/2005 |
| JP | A-2006-208098 | 8/2006 |
| JP | 2006-343193 A | 12/2006 |
| JP | A-2009-042172 | 2/2009 |
| JP | A-2011-196796 | 10/2011 |
| JP | A-2011-220901 | 11/2011 |
| JP | A-2011-237251 | 11/2011 |
| JP | A-2012-021880 | 2/2012 |
| JP | U-3175930 | 5/2012 |
| JP | H09127017 * | 5/2016 |

OTHER PUBLICATIONS

Extended European Search Report dated Mar. 8, 2016 for European Application No. 13846704.8, 11 pages.

* cited by examiner

PACKAGE INSPECTION SYSTEM

CROSS-REFERENCE TO RELATED APPLICATIONS

This application is a continuation application of International Application PCT/JP2013/076983, entitled "Apparatus for Inspecting Packaging Body", filed on Oct. 3, 2013, which claims priority to Japanese Patent Application 2012-229565, filed on Oct. 17, 2012. The contents of these applications are incorporated herein by reference in their entirety.

TECHNICAL FIELD

The present invention relates to a package inspection system capable of determining the relative position of a wrapping and a content of a package through the use of both an electromagnetic-wave detector for detecting X rays or terahertz waves and an optical detector.

RELATED ART

In the process of manufacturing a package containing foods, an inspection system utilizing X rays has been used. Such an inspection system has been mainly used to examine whether or not any foreign body other than foods is present in the package.

If not only the presence of foreign bodies but also the relative position of the wrapping and the content of the package can be accurately determined using image data acquired by the inspection system utilizing X rays, it becomes possible to simultaneously determine whether or not a seal failure is caused by the content caught in a seal of the wrapping or whether or not the content is held in a proper storage position of the wrapping, for example.

However, since the wrapping is formed of a thin packaging material, the outline of the wrapping cannot be detected from the image data acquired by the X-ray sensor, unlike the outline of the content. Therefore, it is difficult to determine the relative position of the content and the wrapping by the inspection system utilizing X rays.

In an X-ray inspection system disclosed in Patent Literature 1: Japanese Unexamined Patent Application Publication No. 2011-196796, data representative of the outline of a package are previously stored in a memory. From an X-ray image of a packaging material of the package, an image of a relatively thick part such as zipper is taken as a reference image. Then, the outline data stored in the memory and the reference image are used to estimate the distance from the zipper image to a seal and reproduce the outline of the packaging material. Then, the estimated positional information of the seal and the image of the content acquired by the X-ray sensor are used to determine whether or not the content is caught in the seal.

Patent Literatures 2 to 4 disclose an inspection system provided with both an X-ray detector and an optical detector.

In the inspection system disclosed in Patent Literature 2: Japanese Unexamined Patent Application Publication No. H05-322803, an image of X rays transmitted through a sample is taken by a camera, while visible light is applied to the same sample and an image of reflected visible light is taken by the same camera, so that the X-ray image and the reflected visible light image are displayed on the same display. In this inspection system, the relative position of a metal plate in the sample, which can be seen only in the X-ray image, and a mark on the surface of the sample, which can be seen only in the reflected visible light image, can be checked on the display.

The inspection system disclosed in Patent Literature 3: Japanese Unexamined Patent Application Publication No. 2006-208098 has an X-ray foreign body detection device equipped with a conveyor belt for conveying an object to be inspected. With the conveyor belt between, the X-ray foreign body detection device has an X-ray source at the upper side and an X-ray line sensor at the lower side. The X-ray foreign body detection device also has a CCD camera for taking an external optical image of an object to be inspected.

This inspection system is configured such that specific identification information such as serial number put on an object to be inspected is obtained by taking the external optical image and a single synthesis inspection image obtained by combining the result of the X-ray inspection with the specific identification information is recorded on an accumulation/record means.

In the inspection system disclosed in Patent Literature 4: Japanese Unexamined Patent Application Publication No. 2009-42172, an image-taking part having an illumination device and a CCD camera and an X-ray inspection part having an X-ray source and an X-ray detector are disposed along a conveyance path of a transport conveyor. A work to be conveyed by the transport conveyor is of a packaging sheet having a plurality of pockets at regular intervals, bonded around the pockets to have seals, and perforated for separation into individual pockets.

In this inspection system, the seal length of the seal can be measured by optical detection with the image-taking part, and the inspection area including the pocket can be determined based on the measured seal length. Then, the inspection is performed to determine whether or not the content detected by the X-ray detector coincides with the pocket.

SUMMARY OF THE INVENTION

Technical Problem to be Solved

In the X-ray inspection system disclosed in Patent Literature 1, since the data representative of the outline of a package to be inspected have to be stored in the memory, the preparatory work prior to the inspection is complicated. In addition, new outline data have to be stored every time the type of a package to be inspected changes, which makes the preparatory work more complicated.

Moreover, when the inspection is performed on a package formed of a packaging material having a thick part such as zipper, the zipper can be taken as a reference image; but when the inspection is performed on a package formed of a generally-thin packaging material not having a zipper, the reference image cannot be acquired from the X-ray image data and therefore, the relative position of the X-ray image data and the outline data cannot be determined, which makes it virtually impossible to accurately reproduce the outline of the packaging material.

On the other hand, Patent Literatures 2 to 4 disclose an inspection system provided with both an X-ray detector and an optical detector.

However, the inspection system disclosed in Patent Literature 2 or 3 is designed to inspect an object with X rays and also acquire an image of a mark or specific identification information displayed on the surface of the object to be inspected through the optical detection with visible light and therefore is not capable of acquiring an entire image of a package so as to check the relative position of the outline of the package and a content.

In the inspection system disclosed in Patent Literature 4, the image-taking part having a CCD camera is located apart from the X-ray inspection part. When a work, e.g., a packaging sheet extending continuously in the conveyance direction is to be inspected, therefore, the work has substantially the same attitude when it is passing the X-ray inspection part and when it is passing the image-taking part. However, if the work is realized in an individual package formed by individually wrapping a content, the work may change in attitude between when it is passing the X-ray inspection part and when it is passing the image-taking part, so that the image acquired by the X-ray inspection part may be different in attitude from the image of the same work acquired by the image-taking part.

Moreover, since any inspection system disclosed in Patent Literatures 2 to 4 is configured such that X rays are allowed to pass through the transport conveyor for detection by the X-ray detector, the transport conveyor slightly appears in the X-ray image. Therefore, if the conveyor belt has a scratch or a foreign body attached thereto, they also appear in the X-ray image and may be erroneously identified as a foreign body in the work.

In any inspection system disclosed in Patent Literatures 2 to 4, furthermore, the light reflected from the work is received as an image to be taken by visible light. Therefore, there is a likelihood that the outline of the wrapping cannot be accurately taken because light reflection varies according to the material of the wrapping of the work.

The present invention is to solve the above-mentioned problem in the prior art and has an object to provide a package inspection system capable of accurately determining the outline of a wrapping and accurately determining the relative position of the outline of the wrapping and a content detected in X-ray image data.

Solution to Problem

The present invention is characterized by comprising: a conveyor mechanism for conveying a package having a content in a wrapping; an irradiation part for irradiating the moving package with an X ray or a terahertz wave; an electromagnetic-wave detection part for detecting the X ray or terahertz wave transmitted through the package; an optical detection part for taking an optical image of the moving package; and a controller, the conveyor mechanism having a gap, an electromagnetic-wave detection image-taking line coinciding with center of a detection area of the electromagnetic-wave detection part and passing through the gap, the controller being configured to determine positional relationship between the wrapping and the content based on first image data obtained from detection output from the electromagnetic-wave detection part and second image data obtained from detection output from optical detection part.

In the package inspection system according to the present invention, since the conveyor mechanism has a gap and the X ray or terahertz wave is allowed to pass through the gap, when image data are taken while the package is passing above the gap, a scratch on a conveyor belt or a foreign body attached to the conveyor belt is prevented from being captured in the image data, making it possible to obtain clear X-ray or terahertz-wave image.

In the present invention, the irradiation part may be provided at one side of the conveyance mechanism, and the electromagnetic-wave detection part may be provided at the other side thereof.

In the present invention, preferably, the optical detection part is configured to detect light passing the package. That is, an illumination part may be provided at one side of the conveyance mechanism, and the optical detection part may be provided at the other side thereof such that an optical detection image-taking line coinciding with center of a detection area of the optical detection part passes through the gap.

The outline image of the package can be accurately obtained by applying light to the package and detecting the light having passed the package with the optical detection part. On the other hand, if the package has a light transmissive wrapping, the content may be inspected only by the optical detection part.

Moreover, if the electromagnetic-wave detection image-taking line and the optical detection image-taking line pass through the same gap, the image data of the content and the image data of the wrapping can be obtained from the package moving in a fixed position at a certain moment, so that the relative position of the content and the wrapping can be determined with high accuracy. For example, the electromagnetic-wave detection image-taking line and the optical detection image-taking line may cross each other in the gap.

In the present invention, the electromagnetic-wave detection image-taking line and the optical detection image-taking line may pass through the gap, and the optical detection image-taking line may be reflected by a reflection member to extend toward the optical detection part.

In this case, the electromagnetic-wave detection image-taking line and the optical detection image-taking line coincide with each other in the gap. Alternatively, the electromagnetic-wave detection image-taking line and the optical detection image-taking line are parallel to each other in the gap.

In the present invention, the electromagnetic-wave detection part and the optical detection part may be located apart from each other in a moving direction of the package, and a position sensor may be provided upstream of these detection parts, enabling the first image data and the second image data to coincide in relative position with each other based on detection output from the position sensor.

The conveyor mechanism may be separated into an upstream conveyor mechanism and a downstream conveyor mechanism such that the gap lies in between the upstream conveyor mechanism and the downstream conveyor mechanism.

In the present invention, preferably, a wave path length from a package conveyance reference plane to the irradiation part is equal to a light path length from the conveyance reference plane to the optical detection part.

In the present invention, preferably, the electromagnetic-wave detection part and the optical detection part are located in an electromagnetic-wave shielding zone.

The judgment section is configured to determine positional relationship between the wrapping and the content by superposing the first image data and the second image data. Alternatively, the judgment section is configured to determine positional relationship between the wrapping and the content by comparing the first image data and the second image data.

As a result, whether or not the content is caught in a seal of the wrapping can be determined at the judgment section.

Alternatively, whether or not the content is properly enclosed in the wrapping can be determined at the judgment section.

The present invention may further include a display unit and enable the display unit to display a superimposed image obtained from the first image data and the second image data. Alternatively, it may be controlled to display either an image obtained from the first image data or an image obtained from the second image data.

Advantageous Effects of Invention

According to the present invention, while the package is moving, the optical image data of the wrapping can be obtained in addition to the X-ray or terahertz-wave image data of the content. Therefore, the relative position of the content and the wrapping of the package can be accurately determined by using two types of image data.

Resultantly, this makes it possible to determine whether or not the content is caught in a seal of the wrapping or the content is certainly enclosed in a predetermined part of the wrapping, even if the wrapping is formed of a thin packaging material.

Moreover, since the conveyor mechanism has a gap and the X ray or terahertz wave is allowed to pass through the gap, when image data are taken while the package is passing above the gap, a scratch on a conveyor belt or a foreign body attached to the conveyor belt is prevented from being captured in the image data, whereby clear X-ray or terahertz-wave image can be obtained.

DETAILED DESCRIPTION OF EMBODIMENTS

Figure 1:
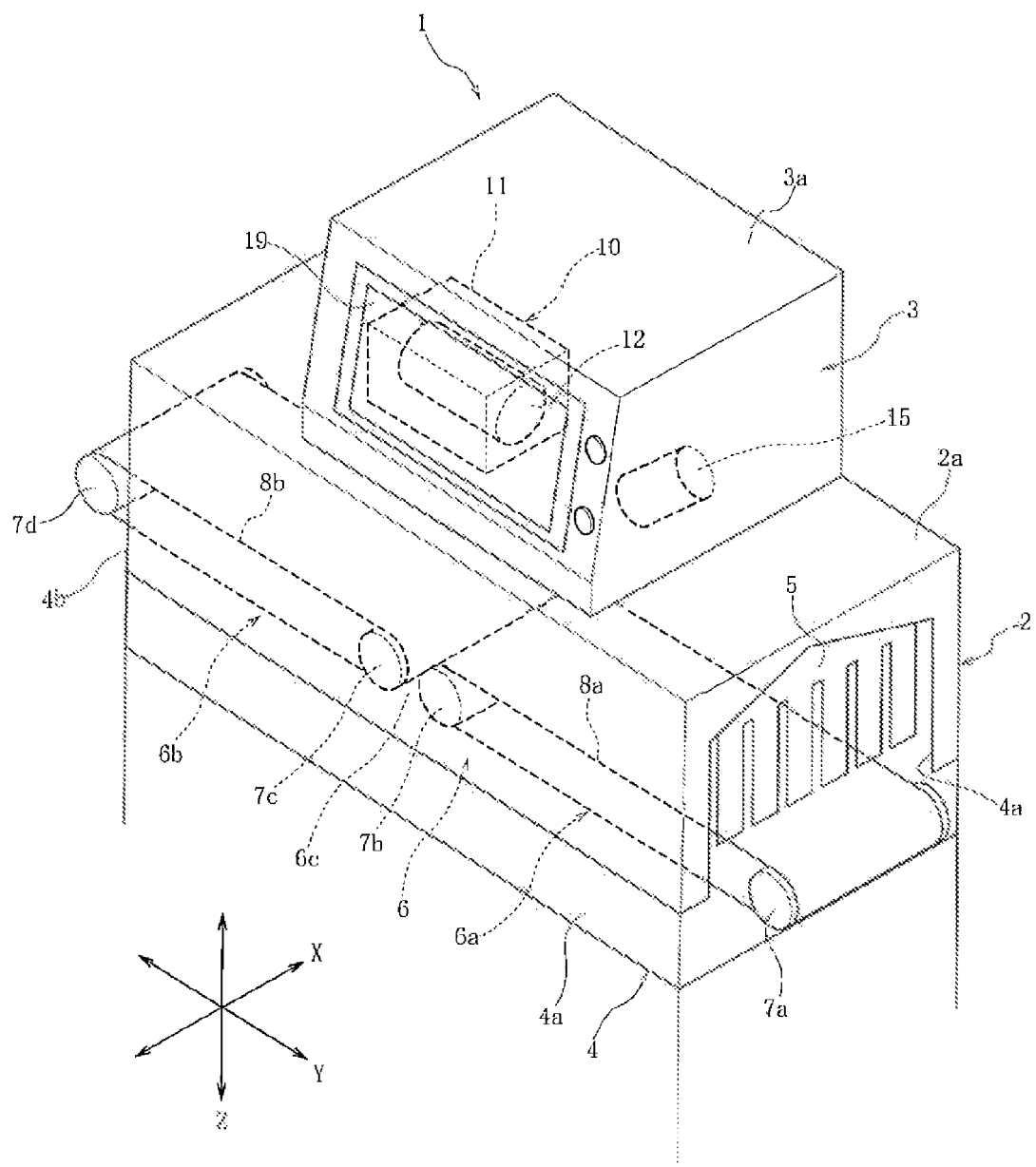
FIG. 1 is a perspective view showing the appearance of a package inspection system according to a first embodiment of the present invention.

As shown in FIG. 1, an inspection system 1 according to a first embodiment of the present invention has a package conveyance zone 2, an overlying upper housing 3, and a lower housing 4 placed below the package conveyance zone 2.

The package conveyance zone 2 is formed inside an intermediate enclosure 2a. The intermediate enclosure 2a has an inlet 4a at one end and an outlet 4b at the other opposite end. Each of the inlet 4a and the outlet 4b is provided with an X-ray shielding sheet 5, so that the package conveyance zone 2 inside the intermediate enclosure 2a becomes an electromagnetic-wave shielding zone (X-ray shielding zone).

Figure 2:
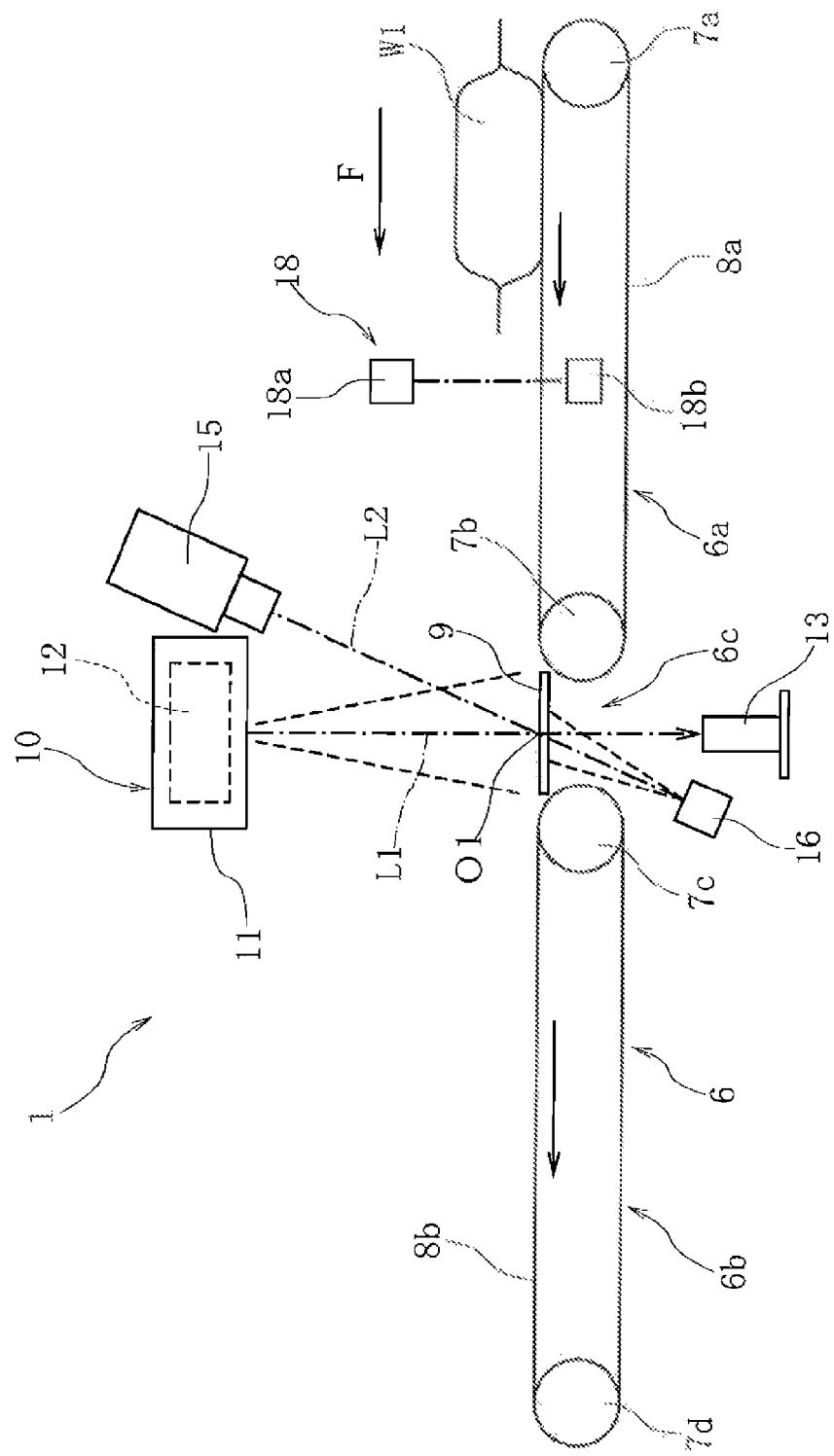
FIG. 2 is a front view showing the internal construction of the package inspection system according to the first embodiment.

A conveyor mechanism 6 is provided in the package conveyance zone 2. As shown in FIGS. 1 and 2, the conveyor mechanism 6 is separated into an upstream conveyor mechanism 6a and a downstream conveyor mechanism 6b, forming a gap 6c at which a space is left between the upstream conveyor mechanism 6a and the downstream conveyor mechanism 6b in the moving direction.

The upstream conveyor mechanism 6a has an upstream roller 7a and a downstream roller 7b with a conveyor belt 8a wound around between the rollers 7a and 7b. One of the upstream roller 7a or the downstream roller 7b is of a driving roller and the other is of a driven roller. The downstream conveyor mechanism 6b has an upstream roller 7c and a downstream roller 7d with a conveyor belt 8b wound around between the rollers 7c and 7d. One of the upstream roller 7c or the downstream roller 7d is provided to work as a driving roller and the other is a driven roller.

The upstream conveyor belt 8a is a light transmissive belt. For example, it is a transparent or semi-transparent belt made of a synthetic resin or a rubber belt having a large number of apertures regularly arranged therein. The downstream conveyor belt 8b may be a light transmissive one or a light non-transmissive one.

The upstream conveyor belt 8a and the downstream conveyor belt 8b travel around at the same speed. With the upstream conveyor belt 8a travelling around, a package W1 put on an upstream end of the upstream conveyor belt 8a is brought into the package conveyance zone (electromagnetic-wave shielding zone) 2 through the inlet 4a and conveyed at a constant speed leftward in the drawing (in the F direction). Then, after passing the gap 6c, the package W1 is received by the downstream conveyor belt 8b and brought out of the outlet 4b with the conveyor belt 8b travelling around.

In FIG. 1, the moving direction (F direction) of the package W1 is set as Y direction, and the direction perpendicular to the moving direction (F direction) is set as X direction. On the other hand, the direction perpendicular to the moving direction (F direction) is set as Z direction.

As shown in FIG. 2, a transfer plate 9 is placed at the gap 6c between the upstream conveyor mechanism 6a and the downstream conveyor mechanism 6b. The transfer plate 9 employs a transparent or semi-transparent synthetic resin plate that is formed of a material transmissive to X rays and light at a thickness that does not prevent the transmission. With the transfer plate 9, the package W1 being transferred from the upstream conveyor belt 8a to the downstream conveyor belt 8b can be easily kept in an almost horizontal position at the gap 6c.

The upper housing 3 has an upper enclosure 3a, and an X-ray generator 10 is housed in the upper enclosure 3a. The X-ray generator 10 has an X-ray tube 12 housed in a sealed container 11. The lower housing 4 has a lower enclosure 4a, and an X-ray sensor 13 is housed therein. The X-ray sensor 13 is of a line sensor, in which an X-ray detection element extends linearly or elements are arranged linearly in the X direction perpendicular to the moving direction of the package W1 so as to form an X-ray detection line. The X-ray sensor 13 may have either a single or a plurality of X-ray detection lines extending in the X direction.

In the present embodiment, the X-ray tube 12 is used as an electromagnetic-wave irradiation part, and the X-ray sensor 13 is used as an electromagnetic-wave detection part. However, the electromagnetic-wave irradiation part may irradiate terahertz waves, and the electromagnetic-wave detection part may be composed of elements capable of detecting terahertz waves transmitted through the package W1.

In FIG. 2, the centerline of the X-ray detection area in which X rays can be detected by the X-ray sensor 13 (X-ray detection image-taking line) is indicated by L1. The X-ray detection image-taking line (electromagnetic-wave detection image-taking line) L1 is in a line shape joining the center of the X-ray generator 10 and the center of the X-ray sensor 13. Moreover, the X-ray detection image-taking line represents a detection plane parallel to the X-Z plane rising vertically from the X-ray detection line of the X-ray sensor 13 being a line sensor, and therefore can be restated as X-ray detection image-taking plane. As shown in FIG. 2, the X-ray detection image-taking line L1 of the X-ray sensor 13 passes through the gap 6c of the conveyor mechanism 6 and extends in the Z direction perpendicular to the Y direction being the moving direction of the package W1.

As shown in FIG. 2, in the upper housing 3, an optical sensor 15 is provided as an optical detection part; in the lower housing 4, an illumination part 16 is provided facing the optical sensor 15. The optical sensor 15 employs a line sensor, in which a light detection element extends linearly or elements are arranged linearly in the X direction perpendicular to the moving direction of the package W1 so as to form a light detection line. The optical sensor 15 may have either a single or a plurality of light detection lines extending in the X direction.

In FIG. 2, the centerline of the light detection area in which light can be detected by the optical sensor 15 (light detection image-taking line) is indicated by L2. The light detection image-taking line L2 is in a line shape joining the center of the optical sensor 15 and the center of the illumination part 16. Moreover, the light detection image-taking line L2 represents a detection plane extending from the light detection line of the optical sensor 15 with a depth in the X direction, and therefore can be restated as light detection image-taking plane. As shown in FIG. 2, the light detection image-taking line L2 of the optical sensor 15 being a line sensor passes through the gap 6c of the conveyor mechanism 6 and is inclined at an angle of less than 90 degrees with respect to the Z direction perpendicular to the moving direction of the package W1.

As shown in FIG. 2, the X-ray image-taking line L1 and the light detection image-taking line L2 cross each other in the same gap 6c. The intersection O1 of the X-ray image-taking line L1 and the light detection image-taking line L2 is located on the surface of the transfer plate 9, i.e., the conveyance reference plane of the conveyor mechanism 6 (the plane joining the upper surface of the conveyor belt 8a and the upper surface of the conveyor belt 8b) or located above the conveyance plane within the range of the thickness of the package W1.

As shown in FIG. 2, a position sensor 18 forming a position detection part is provided in the upstream conveyor mechanism 6a. The position sensor 18 employs an optical sensor composed of a light-emitting part 18a and a light-receiving part 18b facing each other. With the conveyance path of the package W1 between, the light-emitting part 18a is placed at the upper or lower side thereof, and the light-receiving part 18b faces it at the other side thereof.

As shown in FIG. 1, a display unit 19 and a control panel are provided at the front part of the upper enclosure 3a constituting the upper housing 3. The display unit 19 may be composed of a display panel such as color liquid crystal panel and its driving circuit. Various types of operation buttons are arranged on the control panel.

Figure 10:
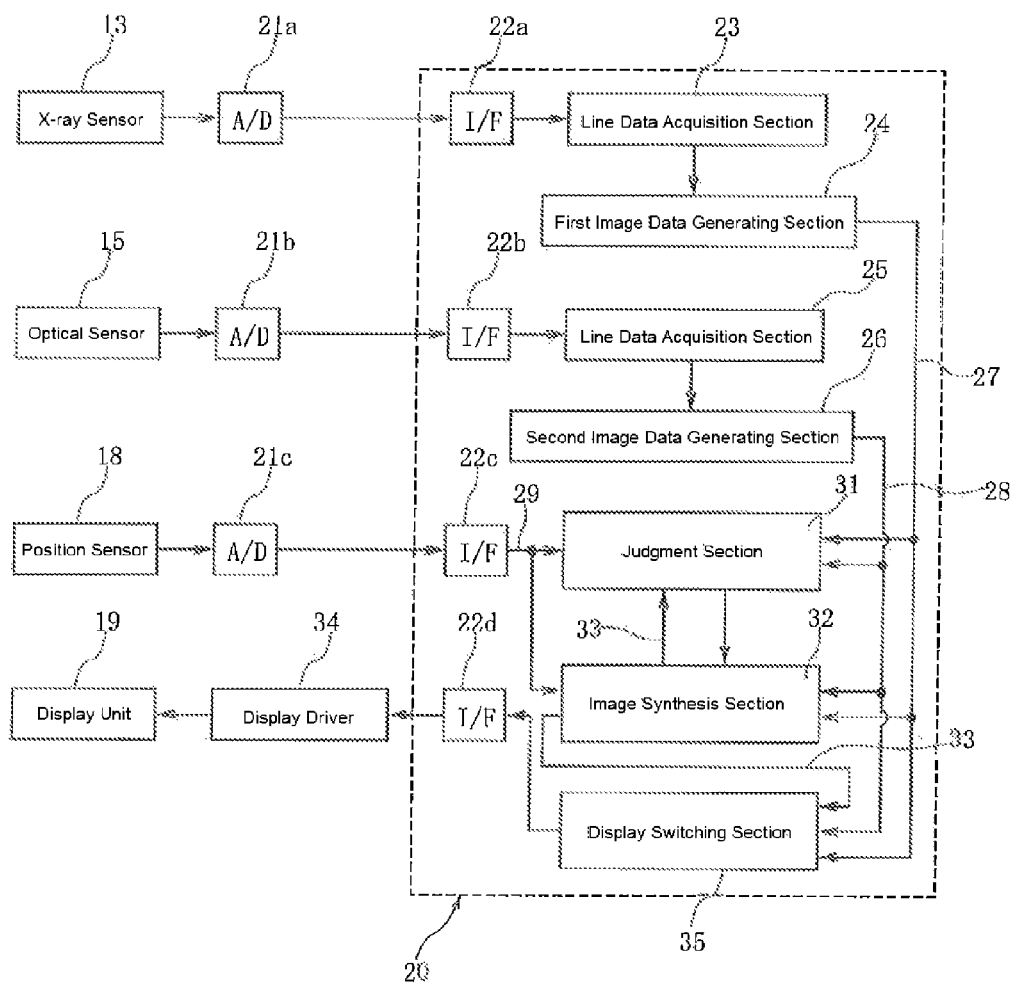
FIG. 10 is a circuit block diagram of an inspection system according to the present invention.

FIG. 10 shows a circuit block diagram illustrating the outline of an electronic circuit provided in the inspection system 1.

A controller 20 may be composed of a CPU and a memory; the blocks inside the controller 20 shown in FIG. 10 can be configured by executing software installed in the CPU.

Detection output from the X-ray sensor 13 can be converted into digital signals at an A/D converter 21a and sent to a line data acquisition section 23 of the controller 20 via an input interface 22a. At the line data acquisition section 23, density data detected at the X-ray detection line of the X-ray sensor 13 can be acquired on a line-by-line basis. The density data for each line acquired at the line data acquisition section 23 can be sent to and accumulated at a first image data generating section 24, thereby generating a first image data 27 composed of single picture density data.

Detection output from the optical sensor 15 can be converted into digital signals at an A/D converter 21b and sent to a line data acquisition section 25 of the controller 20 via an input interface 22b. At the line data acquisition section 25, density data detected at the light detection line of the optical sensor 15 can be acquired on a line-by-line basis. The density data for each line acquired at the line data acquisition section 25 can be sent to and accumulated at a second image data generating section 26, thereby generating a second image data 28 composed of single picture density data.

As shown in FIG. 10, the first image data 27 generated at the first image data generating section 24 as a density image from the X-ray detection output can be sent to a judgment section 31, an image synthesis section 32 and a display switching section 35. The second image data 28 generated at the second image data generating section 26 as a density image from the light detection output can also be sent to the judgment section 31, the image synthesis section 32 and the display switching section 35. The judgment section 31 and the image synthesis section 32 allow data interchanges or exchanges between each other.

Detection output from the position sensor 18 can be converted into digital signals at an A/D converter 21c and sent to the judgment section 31 and the image synthesis section 32 as timing signals 29 via an input interface 22c.

At the image synthesis section 32, the first image data 27 and the second image data 28 are superimposed together. Superimposed image data 33 obtained by combining two types of image data can be sent to the display switching section 35. The superimposed image data 33 can also be sent to the judgment section 31.

The display switching section 35 is operable to switch by operating one of the operation buttons on the display panel. The superimposed image data 33 or the first image data 27 or the second image data 28 can be chosen by the display switching section 35 and sent to a display driver 34 via an output interface 22d. The display unit 19 can be driven by the display driver 34 so that the screen of the display panel can display an image based on the superimposed image data 33. Alternatively, the screen can display an image based on the first image data 27 or an image based on the second image data 28.

Then, the inspection procedure of the package W1 using the inspection system 1 will be described hereinbelow.

Figure 11A:
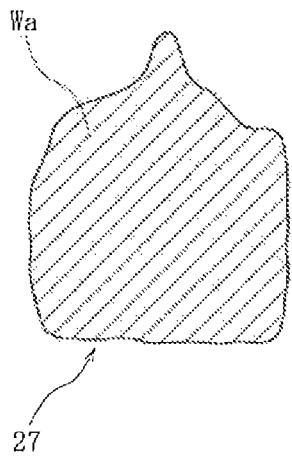
FIG. 11(A) shows a first image data of a content acquired by an inspection system according to the present invention.
Figure 11B:
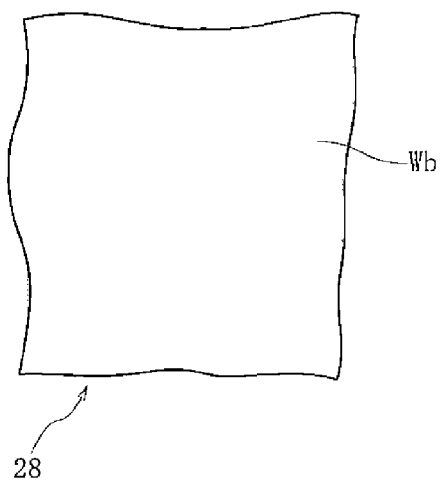
FIG. 11(B) shows a second image data of a wrapping acquired by an inspection system according to the present invention.
Figure 11C:
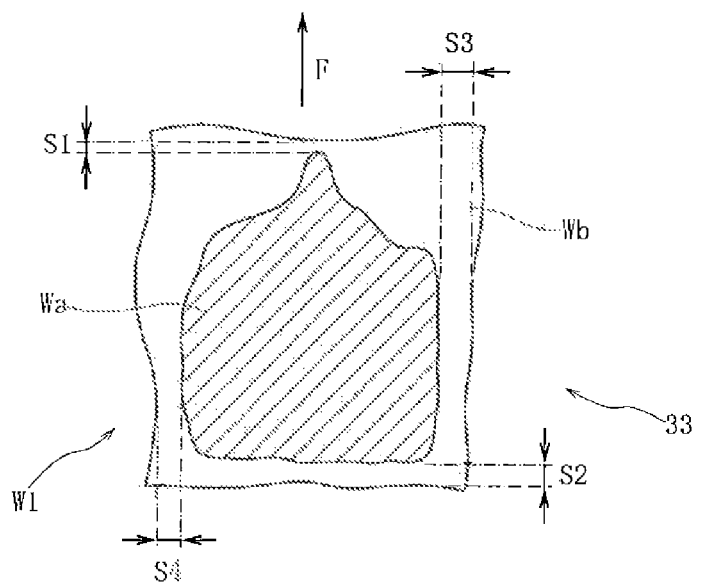
FIG. 11(C) shows a superimposed image data produced by superimposing the first image data of FIG. 11(A) and the second image data of FIG. 11(B)

The package W1, which is formed by enclosing a content Wa in a wrapping Wb as shown in FIG. 11(C), is conveyed in the F direction by the conveyor belt 8a of the upstream conveyor mechanism 6a, passed over the transfer plate 9 at the gap 6c and received by the conveyor belt 8b of the downstream conveyor mechanism 6b.

The wrapping Wb of the package W1 employs a bag that is formed of a synthetic resin film that is subjected to printing and therefore cannot be optically seen through, a bag that is formed of a thin metal foil such as aluminum foil and therefore cannot be optically seen through or a bag that is formed of a laminate of a metal foil and a synthetic resin film and therefore cannot be optically seen through. Alternatively, it may be a bag enclosing a tray formed of a thin synthetic resin material.

The content Wa of the package W1 may be of snack confectionary, processed food for retort pouch, processed meat or fish or fresh food.

When the package W1 being conveyed by the conveyor mechanism 6 passes the position sensor 18, the timing signal 29 obtained from the detection output is sent to the judgment section 31 and the image synthesis section 32 shown in FIG. 10.

When the package W1 passes the gap 6c of the conveyor mechanism 6, the package W1 is irradiated with the X rays emitted from the X-ray generator 10, so that the X rays transmitted through the package W1 can be detected by the X-ray sensor 13. Moreover, infrared light or visible light such as LED light is applied to the gap 6c from the illumination part 16, so that the light can be detected by the optical sensor 15.

The detection output from the X-ray sensor 13 is sent to the line data acquisition section 23 of the controller 20 shown in FIG. 10, and the line image data are accumulated at the first image data generating section 24 to generate the first image data 27. Since the wrapping Wb of the package W1 is formed of a thin packaging material, a large amount of X rays can be transmitted. On the other hand, the content, since thick in thickness, reduces the amount of X-ray transmission. The first image data 27 show the density contrast of the detected amount of X rays; the first data image includes image data showing the outline of the content Wa, as illustrated in FIG. 11(A), but does not substantially include image data showing the outline of the wrapping Wb shown in FIG. 11(B).

The detection output from the optical sensor 15 is sent to the line data acquisition section 25 of the controller 20, and the line image data are accumulated at the second image data generating section 26 to generate the second image data 28. Since the wrapping Wb of the package W1 is formed of a light non-transmissive packaging material, the second image data 27 include an image showing the outline of the wrapping Wb, as illustrated in FIG. 11(B), but do not include an image showing the outline of the content Wa.

When the package W1 being conveyed in the F direction by the conveyor mechanism 6 is detected by the position sensor 18, the timing signal 29 teaching the detection timing is sent to the judgment section 31 and the image synthesis section 32.

The controller 20 has a counter which begins to measure the passage of time from the moment of receiving the timing signal 29 due to detection of the package W1. Alternatively, the counter may begin to count the number of lines of the line image data obtained from the X-ray sensor 13 and the line image data obtained from the optical sensor 15 from the moment of receiving the timing signal.

At the judgment section 31 and the image synthesis section 32, the first image data 27 and the second image data 28 are acquired at the same timing based on the timing signal. In other words, the image data are acquired such that the image data of the content Wa included in the first image data 27 coincide in relative position with the image data of the wrapping Wb included in the second image data 28.

It should be noted that when the package W1 on the conveyor mechanism 6 is being conveyed with its side edge inclined with respect to the X direction, the first image data 27 and the second image data 28 can be amended to correct the inclination within the X-Y coordinate plane such that the side of the package W1 in the image extends along the X direction.

FIG. 11(C) shows a superimposed image data 33 produced at the image synthesis section 32. The superimposed image data 33 are produced by superposing the first image data 27 and the second image data 28 to occupy the same position based on the timing signal from the position sensor 18. In the superimposed image data 33, the positional relationship between the image of the content Wa and the image of the wrapping Wb shows accurately the same positional relationship as in the moving package W1. After the selection by the display switching section 35, the superimposed image data 33 shown in FIG. 11(C) are sent to the display driver 34 and displayed on the display screen of the display unit 19.

At the judgment section 31 of the controller 20, the data about the relative position of the image data of the content Wa and the image data of the wrapping Wb are calculated based on the superimposed image data 33 produced at the image synthesis section 32. In the example shown in FIG. 11(C), calculated are the minimum distance S1 between the front edge of the wrapping Wb and the content Wa, the minimum distance S2 between the rear edge of the wrapping Wb and the content Wa, the minimum distance S3 between the right edge of the wrapping Wb and the content Wa, and the minimum distance S4 between the left edge of the wrapping Wb and the content Wa.

Whether or not a part of the content Wa is caught in a seal of the wrapping Wb can be determined by obtaining the minimum distances S1, S2, S3 and S4. In the example shown in FIG. 11(C), it is determined that since the minimum distance S1 between the front edge of the wrapping Wb and the content Wa is smaller than a predetermined threshold, there is noticed a high possibility that at the front edge of the wrapping Wb, a part of the content Wa is caught in a seal in which the packaging materials are bonded together, causing a seal failure.

At the judgment section 31 of the controller 20, the relative position of the content Wa and the wrapping Wb may also be determined such that the parameters S1, S2, S3 and S4 are calculated by comparing two types of image data 27 and 28 merely on data without superposing and combining the first image data 27 and the second image data 28.

For example, at the judgment section 31, a first group of coordinate points composed of a plurality of coordinate points indicating the outline of the content Wa included in the first image data 27 are determined on the X-Y coordinates based on the timing signal from the position sensor 18; a second group of coordinate points composed of a plurality of coordinate points indicating the outline of the wrapping Wb included in the second image data 28 are also determined on the X-Y coordinates based on the timing signal. Then, the parameters S1, S2, S3 and S4 are calculated by comparing the first group of coordinate points and the second group of coordinate points.

If a foreign body other than the normal content Wa, e.g., a piece of metal is present in the wrapping Wb of the package W1, furthermore, the foreign body in the first image data 27 can be fetched and recognized as data different in density from the content Wa. At the judgment section 31, therefore, it is possible to determine the position and size of the foreign body. In the inspection system 1, accordingly, the positional relationship between the content Wa and the wrapping Wb can be determined and the presence of the foreign body can also be detected by using the first image data 27 and the second image data 28.

Figure 12A:
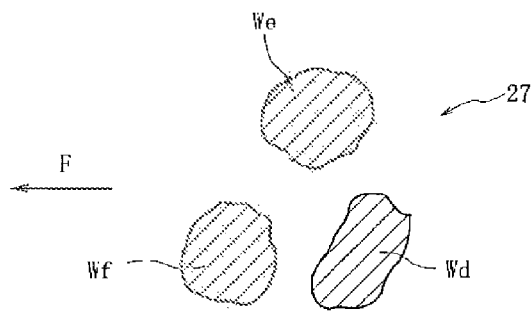
FIG. 12(A) shows a first image data of a content acquired by an inspection system according to the present invention.
Figure 12B:
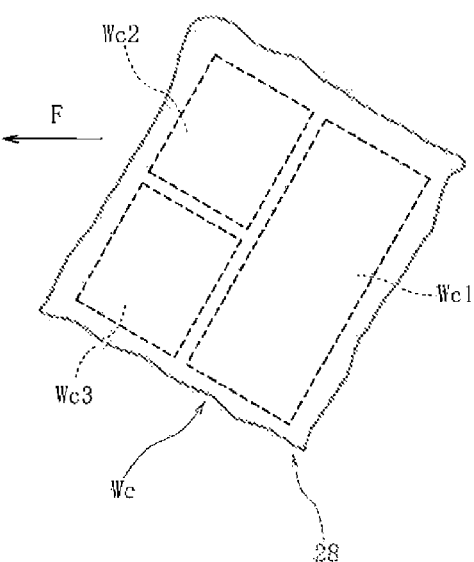
FIG. 12(B) shows a second image data of a wrapping acquired by an inspection system according to the present invention.
Figure 12C:
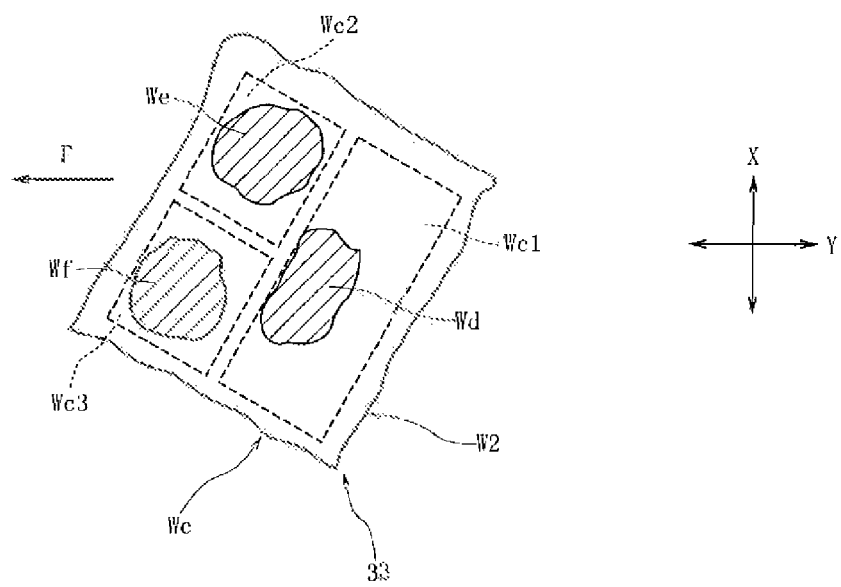
FIG. 12(C) shows a superimposed image data produced by superimposing the first image data of FIG. 12(A) and the second image data of FIG. 12(B)

FIGS. 12(A) to 12(C) show image data of a package W2 having a different configuration.

The wrapping Wc of the package W2 is formed of a light non-transmissive packaging material and partitioned into three storage spaces Wc1, Wc2 and Wc3. Contents Wd, We and Wf may be different in such as food material, and when the package W2 is normal, the content Wd is stored in the storage space Wc1, the content We is stored in the storage space Wc2, and the content Wf is stored in the storage space Wc3.

FIGS. 12(A) to 12(C) show image data at the time when the package W2 is being conveyed with its side edge inclined with respect to the moving direction (F direction).

FIG. 12(A) shows the first image data 27 of the package W2 obtained from the X-ray sensor 13. The first image data 27 include the image data showing the outline of the contents Wd, We and Wf but do not include the image data showing the outline of the wrapping Wc. In the first image data 27 shown in FIG. 12(A), since the image data of the three kinds of contents Wd, We and Wf are arranged in an inclined state with respect to the moving direction (F direction), it is impossible to determine whether or not the three kinds of contents Wd, We and Wf are separately put in the storage spaces Wc1, Wc2 and Wc3 of the package W2 in the standard order.

At the judgment section 31, therefore, the first data image 27 and the second data image acquired at the same timing are compared with each other based on the timing signal 29 from the position sensor 18, thereby making it possible to determine whether or not the three kinds of contents Wd, We and Wf are separately put in the storage spaces Wc1, Wc2 and Wc3 of the package W2 in the standard order.

At the judgment section, moreover, it is also possible to determine whether or not any one of the storage spaces Wc1, Wc2 and Wc3 of the package W2 is empty.

Furthermore, it is also possible to determine whether or not the contents Wd, We and Wf are caught in seals separating the storage spaces Wc1, Wc2 and Wc3 and simultaneously detect the presence of a foreign body.

In the inspection system 1, the X-ray detection image-taking line L1 passes through the gap 6c between the upstream conveyor mechanism 6a and the downstream conveyor mechanism 6b. Therefore, a scratch on the conveyor belt of the conveyor mechanism 6 or a foreign body attached to the conveyor belt can be prevented from being captured in the first image data 27, so that the image of the scratch or foreign body will never be erroneously identified as a foreign body enclosed in the package W1.

It should be noted that even if the transfer plate 9 placed in the gap 6c has a scratch or a foreign body attached thereto, they appear as noise data always at the same position in the first image data 27, and the noise data can be removed by data correction at the image synthesis section 32 or the judgment section 31, so that they hardly cause detection errors.

Moreover, since the light detection image-taking line L2 passes through the gap 6c, the infrared light or visible light emitted from the illumination part 16 can be applied to the package W1 and the light having passed the package W1 can be detected by the optical sensor 15 to generate the second image data 28. Through the use of the transmitted light, the second image data 28 can be generated with the outline of the wrapping Wb, Wc of the package W1 detected clearly and accurately.

In the inspection system 1, the display switching section 35 is operable to switch by operating one of the operation buttons on the display panel. By this switching, the image only of the first image data 27 or the image only of the second image data 28 can be displayed on the display screen of the display unit 19. Particularly, the image only of the second image data 28 based on the transmitted light from the illumination part 16 can be displayed, whereby when the wrapping Wb is formed of a light transmissive packaging material, whether or not the content is caught in the seal can be determined by obtaining the optical image of the package W1.

In the inspection system 1, accordingly, the image to be chosen may be replaced depending on the type of the wrapping Wb. For example, when the wrapping Wb is a bag that cannot be optically seen through, whether or not the content is caught in the seal or the foreign body is present can be determined by acquiring both the first image data 27 and the second image data 28 and displaying the superimposed image; when the wrapping Wb is formed of a light transmissive packaging material, whether or not the content is caught in the seal or the foreign body is present can be determined from the optical image by acquiring only the second image data 28.

Hereinbelow, other embodiments of the inspection system will be described with reference to FIGS. 3 to 7. In the following, the components different from those in the inspection system 1 according to the first embodiment will be mainly described.

Figure 3:
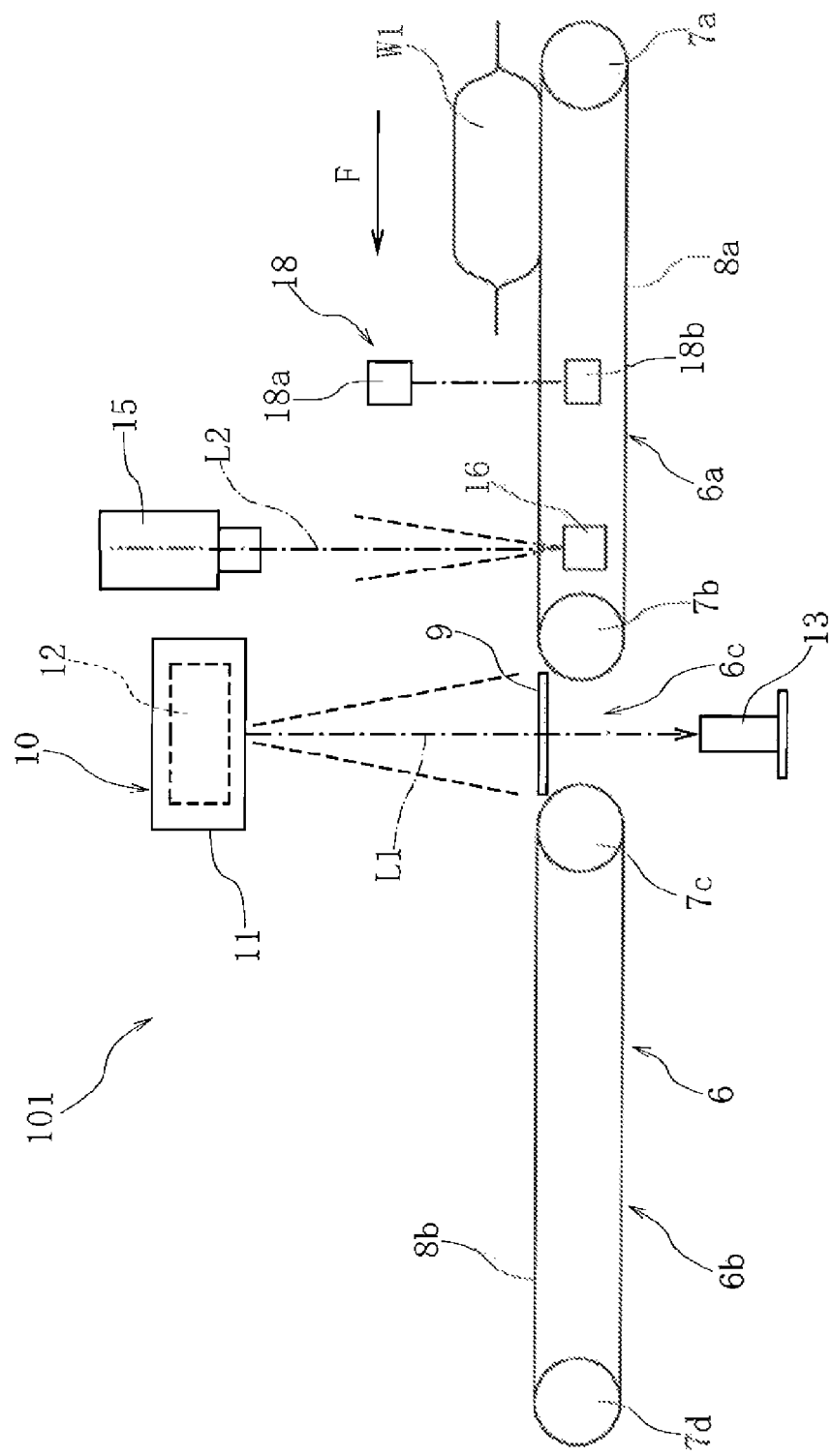
FIG. 3 is a front view showing the internal construction of a package inspection system according to a second embodiment.

In an inspection system 101 according to a second embodiment, as shown in FIG. 3, the illumination part 16 is located inside the upstream conveyor mechanism 6a, and the optical sensor 15 is located right above and faced to the illumination part 16. As a result, the light detection image-taking line L2 of the optical sensor 15 extends perpendicular to the moving direction of the package W1, so that the light detection image-taking line L2 and the X-ray detection image-taking line L1 directed toward the gap 6c extend parallel to each other.

In the inspection system 101 shown in FIG. 3, since the light detection image-taking line L2 extends perpendicular to the moving direction (F direction) of the packaging W1, the shape of the wrapping Wb of the package W1 can be obtained accurately in projection plane form.

Figure 4:
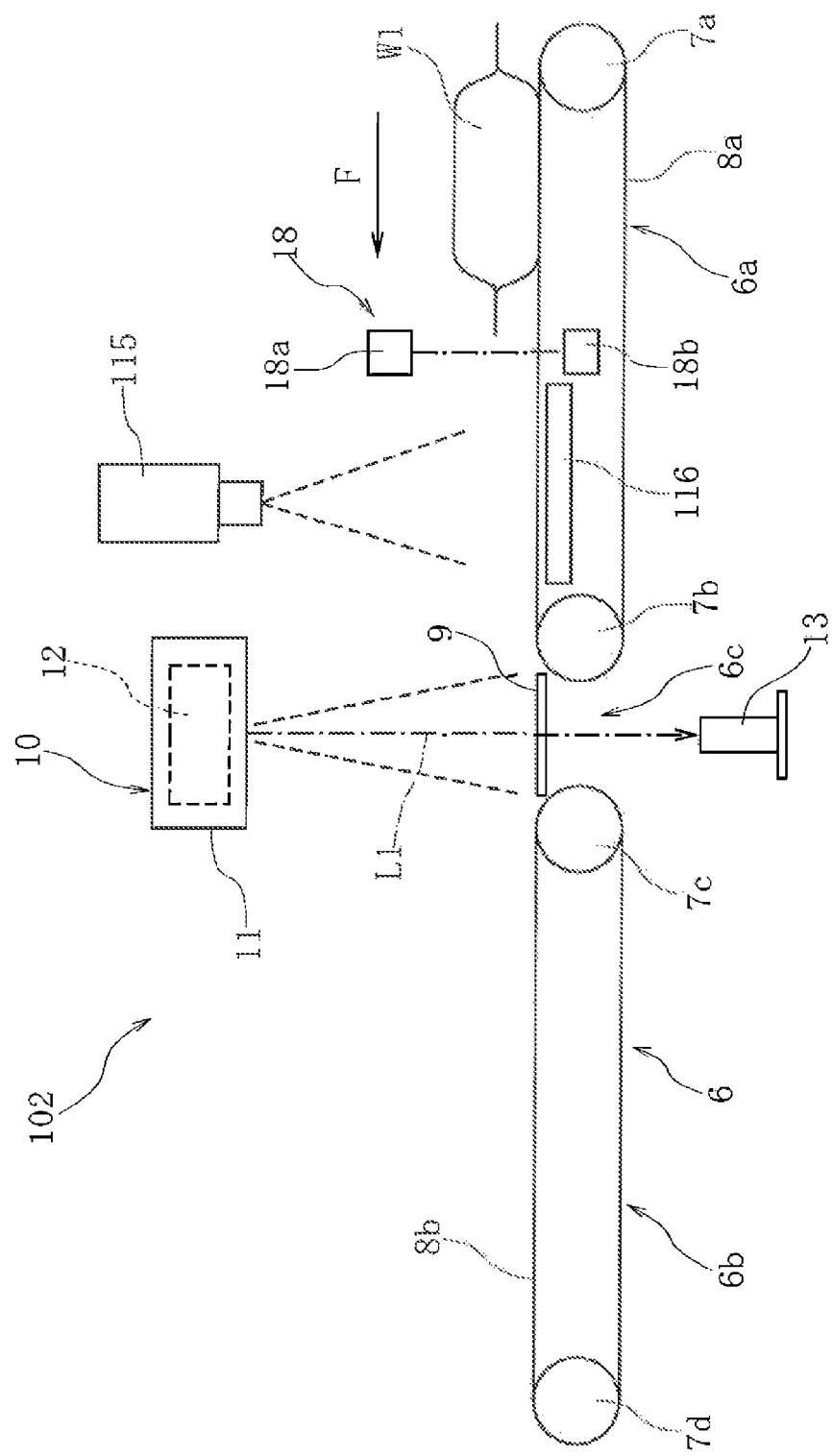
FIG. 4 is a front view showing the internal construction of a package inspection system according to a third embodiment.

In an inspection system 102 according to a third embodiment, as shown in FIG. 4, an optical sensor 115 is located above the upstream conveyor mechanism 6a. This optical sensor 115 employs an area sensor having a number of pixels capable of obtaining a display-sized image at one time rather than a line sensor.

Between upper and lower parts of the conveyor belt of the upstream conveyor mechanism 6a, there is provided an illumination part 116. The illumination part 116 is capable of illuminating a large area including the entire package W1 as the package W1 is passing above the illumination part 116.

In the inspection system 102 shown in FIG. 4, since the entire image of the package W1 can be obtained simultaneously in a bunch by the optical sensor 115, the image processing circuitry in the controller can be simplified.

Figure 5:
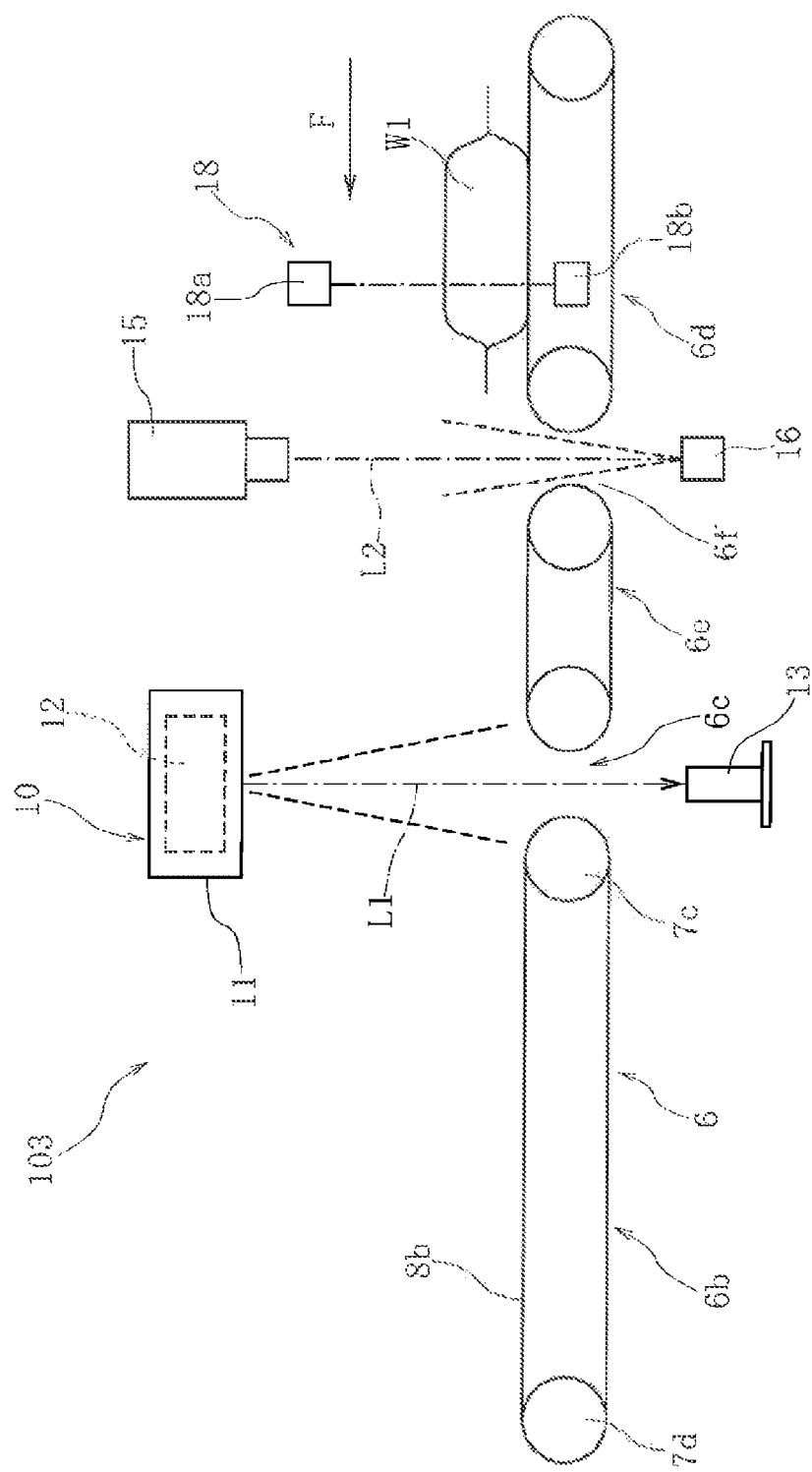
FIG. 5 is a front view showing the internal construction of a package inspection system according to a fourth embodiment.

In an inspection system 103 according to a fourth embodiment, as shown in FIG. 5, the upstream conveyor mechanism is further separated into a first upstream conveyor mechanism 6d and a second upstream conveyor mechanism 6e, forming a gap 6f between the first upstream conveyor mechanism 6d and the second upstream conveyor mechanism 6e.

As in the first embodiment of FIG. 2, the X-ray generator 10 and the X-ray sensor 13, which is of a line sensor, face to each other across the gap 6c between the second upstream conveyor mechanism 6e and the downstream conveyor mechanism 6b, so that the X-ray detection image-taking line L1 passes through the gap 6c. Moreover, the optical sensor 15, which is of a line sensor, and the illumination part 16 face to each other across the gap 6f between the first upstream conveyor mechanism 6d and the second upstream conveyor mechanism 6e, so that the light detection image-taking line L2 of the optical sensor 15 passes through the gap 6f. Furthermore, the X-ray detection image-taking line L1 and the light detection image-taking line L2 extend parallel to each other.

In the embodiment shown in FIG. 5, since only the X-ray sensor 13 faces toward the gap 6c, the distance of the gap 6c can be decreased. Therefore, the transfer plate 9 is not provided for the gap 6c.

If the distance of the gap 6c in the conveyance direction is equal to the distance of the gap 6f in the conveyance direction, conveyance conditions such as change in attitude as the package W1 passes the gap 6f vary little from the conveyance conditions as it passes the gap 6c. This makes it possible for the X-ray sensor 13 and the optical sensor 15 to obtain an image of the same package W1 under almost the same conditions.

Therefore, even though the conveyor mechanism is provided with two gaps 6c and 6f, the consistency can be maintained between the first image data 27 and the second image data 28.

Figure 6:
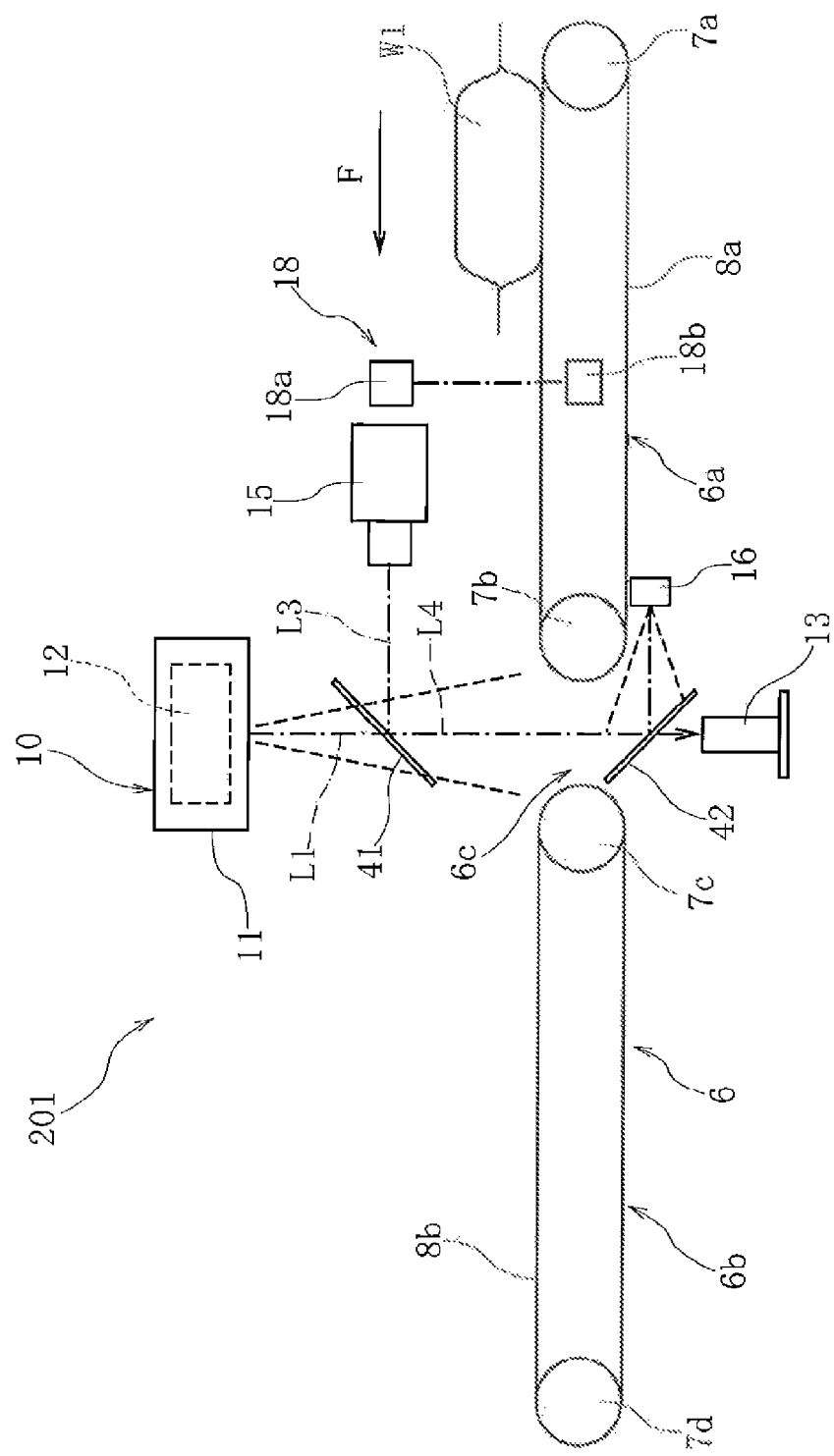
FIG. 6 is a front view showing the internal construction of a package inspection system according to a fifth embodiment.

In an inspection system 201 according to a fifth embodiment, as shown in FIG. 6, the X-ray generator 10 and the X-ray sensor 13 face to each other across the gap 6c between the upstream conveyor mechanism 6a and the downstream conveyor mechanism 6b, and the X-ray detection image-taking line L1 of the X-ray sensor 13 is directed perpendicular to the moving direction (F direction) of the package W1 at the gap 6c.

Above the gap 6c, a reflection member 41 is provided with its reflection surface inclined at an angle of 45 degrees with respect to the X-ray detection image-taking line L1. The light detection image-taking line L3 of the optical sensor 15, which is of a line sensor, is reflected by the reflection member 41, so that the reflected light detection image-taking line L4 coincides with the X-ray detection image-taking line L1 at the gap 6c. Below the gap 6c, moreover, a reflection member 42 is provided such that illumination light emitted from the illumination part 16 can be reflected by the reflection member 42 and applied to the gap 6c.

The reflection members 41 and 42 have an optically reflective surface and are made thin enough to transmit X rays.

In the inspection system 201 shown in FIG. 6, since both the X-ray detection image-taking line L1 and the light detection image-taking line L4 pass through the same gap 6c, the first X-ray image data 27 and the second optical image data 28 of the package W1 can be obtained under the same conditions.

Figure 7:
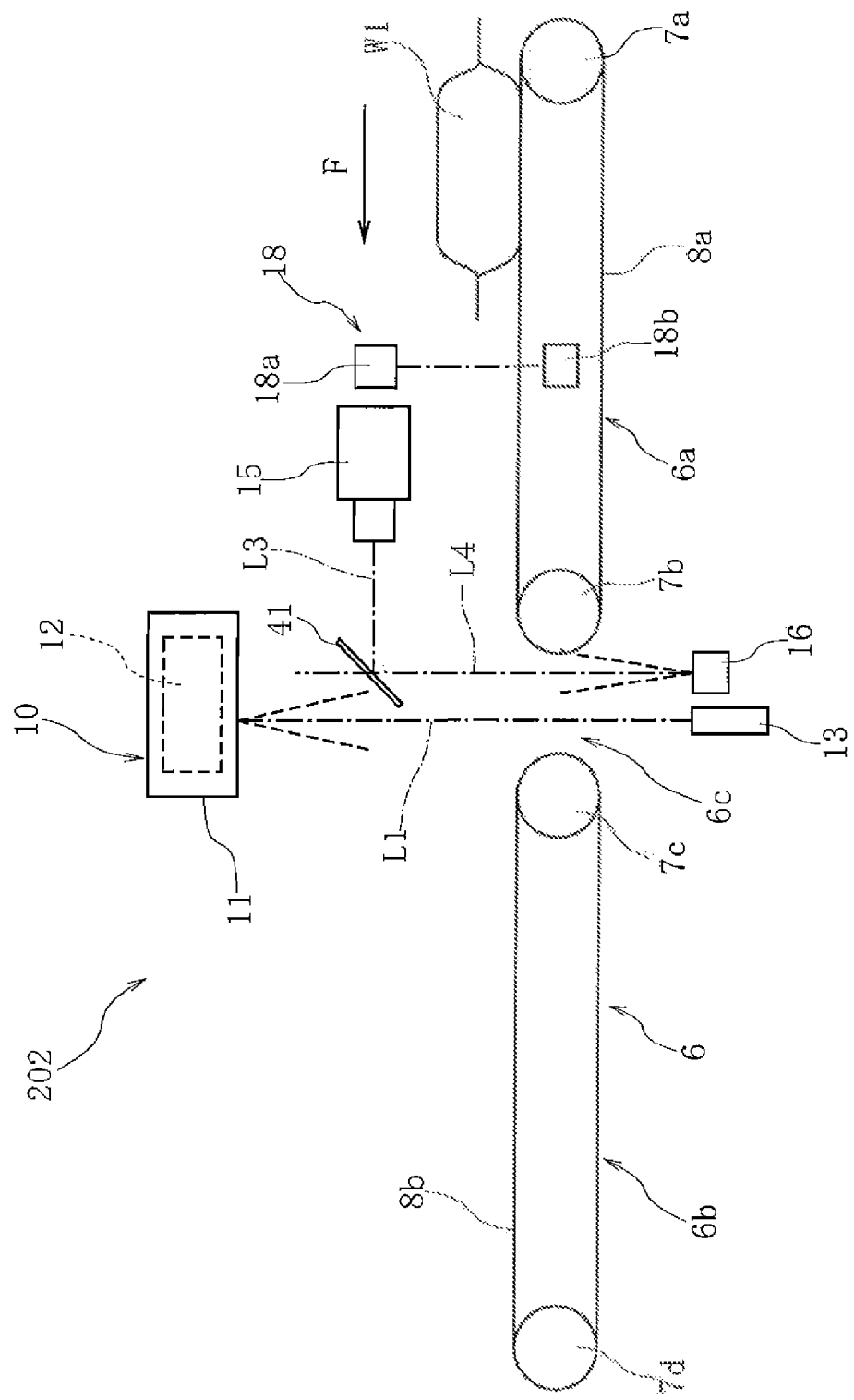
FIG. 7 is a front view showing the internal construction of a package inspection system according to a sixth embodiment.

In an inspection system 202 according to a sixth embodiment, as shown in FIG. 7, the lower reflection member 42 shown in FIG. 6 is removed, and the illumination part 16 is placed alongside the X-ray sensor 13. The X-ray detection image-taking line L1 and the light detection image-taking line L4 extend parallel to each other without coinciding in the gap 6c. The infrared light or visible light emitted from the illumination part 16 passes the package W1 passing above the gap 6c and is then reflected by the reflection member 42 and detected by the optical sensor 15.

In the inspection system 202 shown in FIG. 7, since both the X-ray detection image-taking line L1 and the light detection image-taking line L4 pass through the same gap 6c, the first X-ray image data 27 and the second optical image data 28 of the package W1 passing the gap 6c can be obtained under the same conditions.

In the inspection system 202, the number of reflection members can be reduced as compared with the embodiment shown in FIG. 6. Moreover, since the lower reflection member 42, the reflective surface of which can be easily soiled, is not employed, the detection output from the optical sensor 15 can be kept normal for a long period of time. Moreover, since the upper reflection member 41 does not meet the X-ray detection image-taking line L1, the reflection member 41 can be certainly prevented from being deteriorated by the irradiation of X rays.

It should be noted that the transfer plate 9 is not provided for the gap 6c in the embodiments shown in FIGS. 6 and 7.

Figure 8:
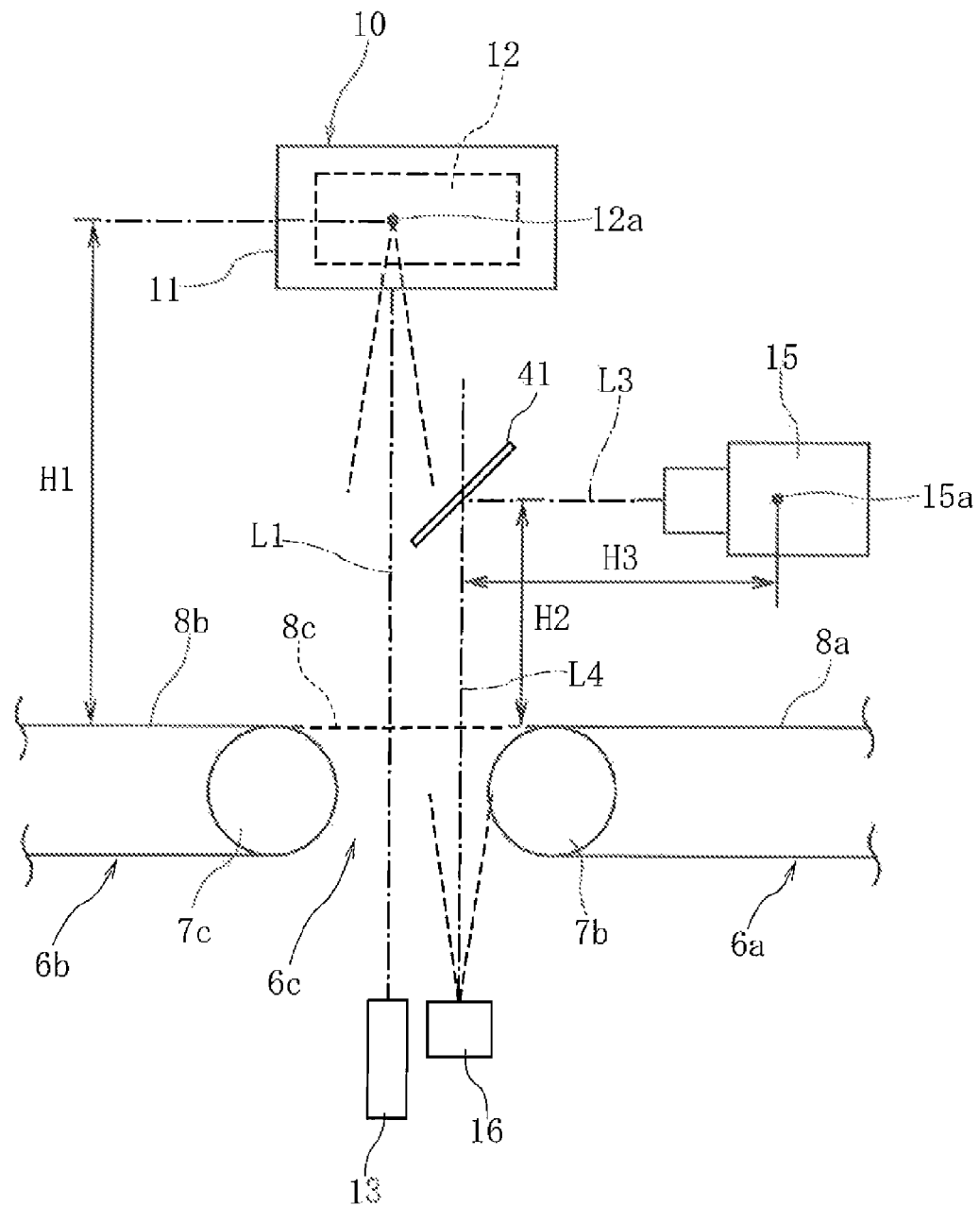
FIG. 8 is an explanatory drawing showing the relationship between wave path length of X rays and light path length of detection light.

In FIG. 8, a wave path length from a conveyance reference plane 8c (plane connecting the upper surface of the conveyor belt 8a and the upper surface of the conveyor belt 8b) to an emission point 12a of the X-ray tube 12 in the inspection system 202 according to the sixth embodiment is indicated by H1, while a light path length from the conveyance reference plane 8c to a detection point 15a of the optical sensor 15 is indicated by H2+H3. Preferably, the wave path length H1 is equal to the light path length H2+H3. It should be noted the term "equal" as used herein means that the dimensions are equal under the condition that the dimensional tolerance or assembly tolerance of components is taken into account, and therefore, they, of course, include tolerance or error (H1≈H2+H3).

Since the package W1 has a certain thickness, if the wave path length H1 is different from the light path length H2+H3, the package W1 varies in shape between the image obtained from the first image data 27 and the image obtained from the second image data 28.

Figure 9:
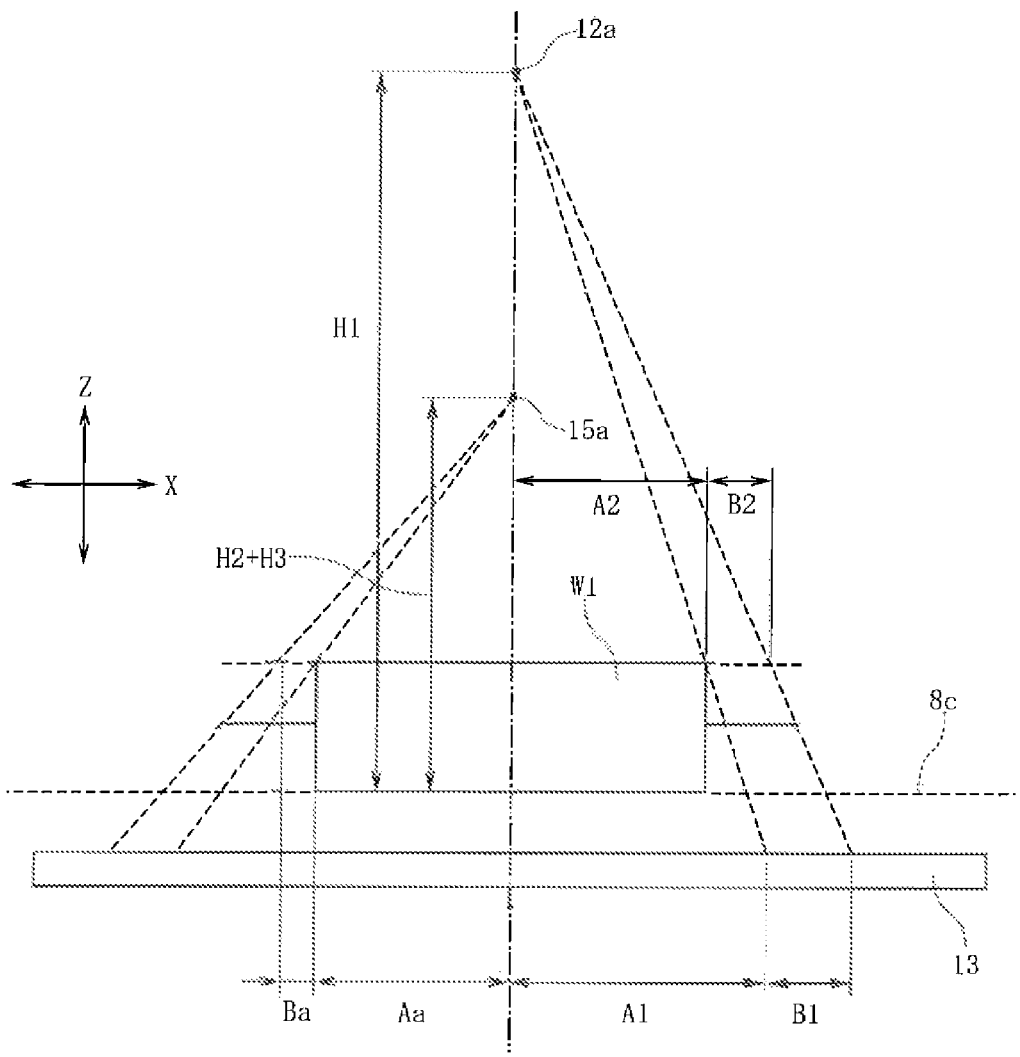
FIG. 9 is an explanatory drawing showing the reason why the wave path length of X rays should be equal to the light path length of detection light.

In FIG. 9, the package W1 lying on the conveyance reference plane 8c and the X-ray sensor 13 are shown in the X-Z plane, wherein the wave path length H1 is different from the light path length H2+H3. In this case, when the image of the package W1 is taken by the X-ray sensor 13, the ratio of the width of the main body to the width of the seal laterally protruding therefrom is A1:B1. On the other hand, when the image of the package W1 is taken by the optical sensor 15, the ratio of the width of the main body to the width of the seal is Aa:Ba, so that the ratio A1:B1 is different from the ratio Aa:Ba.

However, if H1, H2 and H3 satisfy a formula H1=H2+H3 by making the detection point 15a coincide with the emission point 12a, the ratio A1:B1 of the image taken by the X sensor 13 and the ratio A2:B2 of the image taken by the optical sensor 15 become a ratio of bases of similar triangles, whereby the ratio A1:B1 becomes equal to the ratio A2:B2. Therefore, when H1≈H2+H3, the dimensional ratio of components such as main body and seal does not vary between the image from the first image data 27 and the image from the second image data 28.

The preferable relationship between the wave path length H1 and the light path length H2+H3 can be maintained in all the foregoing embodiments.

Figure 13:
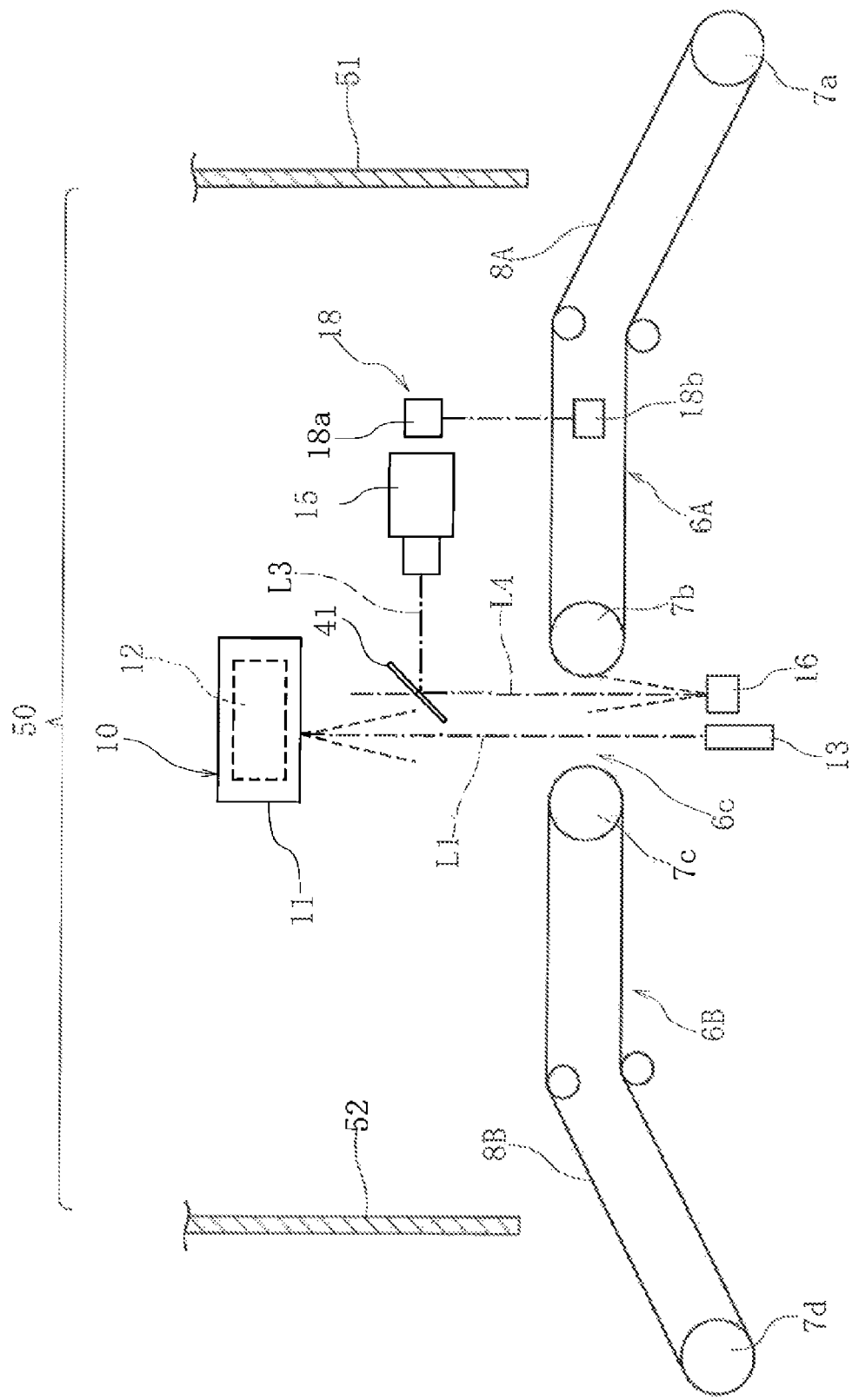
FIG. 13 is an explanatory drawing showing another embodiment of a conveyor mechanism.

In an embodiment shown in FIG. 13, the conveyor belt 8A is inclined upward in the conveyance direction at the upstream part of the upstream conveyor mechanism 6A, while the conveyor belt 8B is inclined downward in the conveyance direction at the downstream part of the downstream conveyor mechanism 6B. Moreover, a shielding plate 51 is provided above the inclined part of the upstream conveyor mechanism 6A, while a shielding plate 52 is provided above the inclined part of the downstream conveyor mechanism 6B, so that an electromagnetic-wave shielding zone (X-ray shielding zone) 50 is formed between the shielding plate 51 and the shielding plate 52.

According to the present invention, both the detection parts, the X-ray detection part having the X-ray sensor 13 and the optical detection part having the optical sensor 15, are placed in the electromagnetic-wave shielding zone (X-ray shielding zone) separated from the outside by the X-ray shielding sheets 5, as shown in FIG. 1, or in the electromagnetic-wave shielding zone (X-ray shielding zone) 50 that is formed by providing the conveyor belts with the inclined parts, as shown in FIG. 13. Since the X-ray detection and the optical detection are performed on the package W1 being conveyed inside the electromagnetic-wave shielding zone (X-ray shielding zone), the package W1 hardly changes in attitude as it moves between two detection parts. Therefore, the image from the first image data 27 and the image from the second image data 28 can easily coincide in attitude.

REFERENCE SIGNS LIST 1, 101, 102, 103, 201, 202 Inspection System
2 Package Conveyance Zone
6 Conveyor Mechanism
6a Upstream Conveyor Mechanism
6b Downstream Conveyor Mechanism
6c, 6f Gap
9 Transfer Plate
10 X-ray Generator (Irradiation Part)
13 X-ray Sensor (Electromagnetic-wave Detection part)
15 Optical Sensor (Optical Detection Part)
16 Illumination Part
18 Position Sensor (Position Detection Part)
19 Display Unit
20 Controller
24 First Image Data Generating Section
26 Second Image Data Generating Section
31 Judgment Section
32 Image Synthesis Section
41, 42 Reflection Member
F Moving Direction
L1 X-ray Detection Image-taking Line (Electromagnetic-wave Detection Image-taking Line)
L2 Light Detection Image-taking Line
W1, W2 Package
Wa, Wd, We, Wf Content
Wb, We Wrapping
Wc1, Wc2, Wc3 Storage Space

What is claimed is:

1. A package inspection system comprising:
a conveyor mechanism for conveying a package having a content in a wrapping whose outline can be visually recognized;
a radiation part for irradiating the moving package with an X ray or a terahertz wave;
an electromagnetic-wave detection part for detecting the X ray or terahertz wave transmitted through the package, the electromagnetic-wave detection part being configured to acquire a first image data defining an outline of the content of the package;
an illumination part for illuminating the moving package with light, wherein the content within the wrapping cannot be seen through optically;
an optical detection part for detecting the light having passed the package, the optical detection part being configured to acquire a second image data defining an outline of the wrapping of the package; and
a controller configured to determine positional relationship between the wrapping and the content based on the first image data and the second image data,
the radiation part and the electromagnetic-wave detection part being placed at opposite sides of the conveyor mechanism, the illumination part and the optical detection part being placed at opposite sides of the conveyor mechanism, and the conveyor mechanism having a gap through which the electromagnetic-wave detection part and optical detection part are allowed to acquire the first image data and the second image data, respectively.

2. The package inspection system according to claim 1, wherein the electromagnetic-wave detection part and the optical detection part are located apart from each other in a moving direction of the package, and a position sensor is provided upstream of these detection parts, enabling the first image data and the second image data to coincide in relative position with each other based on detection output from the position sensor.

3. The package inspection system according to claim 1, wherein the conveyor mechanism is separated into an upstream conveyor mechanism and a downstream conveyor mechanism such that the gap lies in between the upstream conveyor mechanism and the downstream conveyor mechanism.

4. The package inspection system according to claim 1, wherein a wave path length from a package conveyance reference plane to the radiation part is equal to a light path length from the conveyance reference plane to the optical detection part.

5. The package inspection system according to claim 1, wherein the electromagnetic-wave detection part and the optical detection part are located in an electromagnetic-wave shielding zone.

6. The package inspection system according to claim 1, wherein the judgment section is configured to determine positional relationship between the wrapping and the content by superposing the first image data and the second image data.

7. The package inspection system according to claim 1, wherein the judgment section is configured to determine positional relationship between the wrapping and the content by comparing the first image data and the second image data.

8. The package inspection system according to claim 1, wherein the judgment section is configured to determine whether or not the content is caught in a seal of the wrapping.

9. The package inspection system according to claim 1, wherein the judgment section is configured to determine whether or not the content is properly enclosed in the wrapping.

10. The package inspection system according to claim 6, further including a display unit and enabling the display unit to display a superimposed image obtained from the first image data and the second image data.

11. The package inspection system according to claim 10, which is controlled to display either an image obtained from the first image data or an image obtained from the second image data.

12. The package inspection system according to claim 1, wherein a reflection member for reflecting the light from the illumination part toward the optical detection part is positioned to permit simultaneous acquisition of the first image data and the second image data.

* * * * *